US011730459B2

(12) United States Patent
Prior et al.

(10) Patent No.: US 11,730,459 B2
(45) Date of Patent: Aug. 22, 2023

(54) SPECIMEN RETRIEVAL DEVICES AND METHODS

(71) Applicant: COVIDIEN LP, Mansfield, MA (US)

(72) Inventors: Scott J. Prior, Shelton, CT (US); Nikolai D. Begg, Wayland, MA (US)

(73) Assignee: Covidien LP, Mansfield, MA (US)

( * ) Notice: Subject to any disclaimer, the term of this patent is extended or adjusted under 35 U.S.C. 154(b) by 1186 days.

(21) Appl. No.: 16/282,639

(22) Filed: Feb. 22, 2019

(65) Prior Publication Data
US 2019/0254643 A1    Aug. 22, 2019

Related U.S. Application Data

(60) Provisional application No. 62/633,744, filed on Feb. 22, 2018.

(51) Int. Cl.
| | |
|---|---|
| *A61B 17/00* | (2006.01) |
| *A61B 17/42* | (2006.01) |
| *A61B 90/40* | (2016.01) |
| *A61B 10/04* | (2006.01) |
| *A61B 17/221* | (2006.01) |

(52) U.S. Cl.
CPC ........ *A61B 10/04* (2013.01); *A61B 17/00234* (2013.01); *A61B 17/221* (2013.01); *A61B 17/42* (2013.01); *A61B 90/40* (2016.02); *A61B 2017/003* (2013.01); *A61B 2017/00287* (2013.01)

(58) Field of Classification Search
CPC .................. A61B 190/40; A61B 17/42; A61B 2017/00287; A61B 2017/003; A61B 2017/4241; A61B 90/40

USPC .......................................................... 606/114
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |

(Continued)

FOREIGN PATENT DOCUMENTS

| | | |
|---|---|---|
| DE | 3542667 A1 | 6/1986 |
| DE | 8435489 U1 | 8/1986 |

(Continued)

*Primary Examiner* — Kankindi Rwego
(74) *Attorney, Agent, or Firm* — Carter, DeLuca & Farrell LLP

(57) ABSTRACT

A specimen retrieval device includes a tubular body defining a longitudinal bore, an articulation shaft disposed within the longitudinal bore of the tubular body, and a specimen receptacle affixed to a support mechanism at the distal portion of the tubular body. In embodiments, the specimen receptacle has two openings which may be used to transfer a tissue specimen from within a patient's body cavity to outside of the patient's body.

15 Claims, 5 Drawing Sheets

(56) References Cited

U.S. PATENT DOCUMENTS

| | | |
|---|---|---|
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |

(56) References Cited

U.S. PATENT DOCUMENTS

| | | |
|---|---|---|
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 10,736,650 B2 * | 8/2020 | Graf .................. A61B 18/1402 |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0103043 A1 * | 4/2013 | Cabrera .......... A61B 17/00234 606/114 |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2016/0324515 A1 * | 11/2016 | Ravikumar ........ A61B 17/3468 |
| 2016/0346000 A1 * | 12/2016 | Abreu .................. A61B 90/92 |
| 2017/0049427 A1 | 2/2017 | Do et al. |
| 2017/0215904 A1 | 8/2017 | Wassef et al. |
| 2017/0224321 A1 | 8/2017 | Kessler et al. |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2014134285 A1 | 9/2014 |
| WO | 2015134888 A1 | 9/2015 |
| WO | 2017189442 A1 | 11/2017 |

* cited by examiner

SPECIMEN RETRIEVAL DEVICES AND METHODS

CROSS-REFERENCE TO RELATED APPLICATIONS

This application claims the benefit of, and priority to, U.S. Provisional Patent Application No. 62/633,744, filed on Feb. 22, 2018, the entire contents of which are hereby incorporated herein by reference.

TECHNICAL FIELD

The present disclosure relates generally to surgical apparatuses and methods for use in minimally invasive surgical procedures, such as endoscopic and/or laparoscopic procedures, and other reduced-access surgical procedures. More particularly, the present disclosure relates to specimen retrieval devices including specimen receptacles having at least two openings to facilitate passage of a tissue specimen therethrough, and methods associated therewith.

BACKGROUND

Minimally invasive surgery, such as endoscopic surgery, reduces the invasiveness of surgical procedures. Endoscopic surgery involves surgery through body walls or naturally occurring orifices, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars or other instruments are utilized for creating incisions through which the endoscopic surgery is performed; in other procedures, naturally occurring orifices are utilized to provide access. Trocar tubes, cannula devices, access ports, and/or tissue guards may be extended into and left in place in the abdominal wall (or other opening) to provide access for endoscopic surgical tools. A camera or endoscope may be inserted to permit visual inspection and magnification of a body cavity. The surgeon can then perform diagnostic and/or therapeutic procedures at the surgical site with the aid of specialized instrumentation, such as grasping devices including a forceps or a tenaculum, cutters, applicators, energy-based tissue-treatment devices, and the like.

When removing certain tissues from the body cavity, for example tumor tissue, it is important that the tumor tissue does not come into contact with healthy or uninvolved tissue. If tumor tissue or tissue parts have to be removed, they may be introduced into an "extraction bag," also sometimes referred to as a "specimen bag," at the site where the tumor or diseased tissue has been detached from the surrounding tissue, after which the specimen bag is withdrawn from the body, thereby minimizing contact of the diseased tissue with healthy tissue.

SUMMARY

Specimen retrieval devices in accordance with the present disclosure include a tubular body having a proximal portion and a distal portion and defining a longitudinal bore between the proximal portion of the tubular body and the distal portion of the tubular body, and a support member pivotably supported on the distal portion of the tubular body. The specimen retrieval devices in accordance with the present disclosure also include an articulation shaft positioned within the longitudinal bore of the tubular body, the articulation shaft having a proximal portion, a distal portion, and an articulation knob supported on the proximal portion of the articulation shaft, the distal portion of the articulation shaft coupled to the support member, wherein movement of the articulation shaft within the longitudinal bore causes pivotable movement of the support member in relation to the tubular body. The specimen retrieval devices in accordance with the present disclosure also include a specimen receptacle supported on the support member at the distal portion of the tubular body, the specimen receptacle including a body defining a first opening that may be opened and closed and a second opening spaced from the first opening.

In aspects, the support member includes a pair of resilient fingers which support the specimen receptacle.

In some aspects, the resilient fingers are positioned adjacent a first mouth of the specimen receptacle to form the first opening of the specimen receptacle when the specimen retrieval device is in a deployed state.

In aspects, the proximal portion of the tubular body has an opening to permit access to the articulation knob.

In some aspects, the proximal portion of the articulation shaft is threaded and the longitudinal bore includes a threaded portion, the proximal portion of the articulation shaft residing in the threaded portion of the longitudinal bore of the tubular body.

In other aspects, rotation of the articulation knob moves the articulation shaft longitudinally to pivotably move the support member.

In aspects, the support member includes a tab and the articulation shaft is coupled to the support member by the tab.

Methods of the present disclosure include introducing a tubular body of a specimen retrieval device having a proximal portion and a distal portion through a body opening; introducing an articulation shaft having a proximal portion, a distal portion, and an articulation knob through the longitudinal bore of the tubular body such that the distal portion of the articulation shaft is coupled to a support member that is pivotably supported about a pivot axis on the distal portion of the tubular body; positioning the distal portion of the tubular body within a body cavity to position a specimen receptacle supported on the support member in the body cavity; actuating the articulation knob of the articulation shaft to articulate the support member about the pivot axis to reposition a first opening of the specimen receptacle in relation to a tissue specimen; removing a second opening of the specimen receptacle from the body cavity; passing the tissue specimen through the first opening of the specimen receptacle into the specimen receptacle and out the second opening; and removing the specimen retrieval device from the body cavity.

In aspects, inserting the specimen retrieval device through the body opening occurs by passing the distal portion of the tubular body through a cannula.

In some aspects, actuating the articulation knob includes rotating a threaded portion of the articulation shaft within a threaded portion of the longitudinal bore to longitudinally move the articulation shaft, thereby articulating the support member.

In aspects, the support member includes a pair of resilient fingers which support the specimen receptacle and open the first opening of the specimen receptacle in a deployed state.

In some aspects, removing the second opening from the body cavity occurs by grasping the specimen receptacle with a grasping device and pulling the second opening out of the body cavity.

In aspects, the grasping device is selected from a forceps, a tenaculum, and combinations thereof.

In some aspects, removing the second opening occurs by pulling the second opening out of a cannula.

In other aspects, removing the second opening occurs by pulling the second opening out of a patient's vagina.

In aspects, passing the tissue specimen through the first opening of the specimen receptacle into the specimen receptacle and out the second opening occurs by utilizing a grasping device to grasp the tissue specimen and pass the tissue specimen through the specimen receptacle.

BRIEF DESCRIPTION OF THE DRAWINGS

Aspects and features of the presently disclosed specimen retrieval device are described hereinbelow with reference to the drawings wherein.

DETAILED DESCRIPTION

Figure 1:
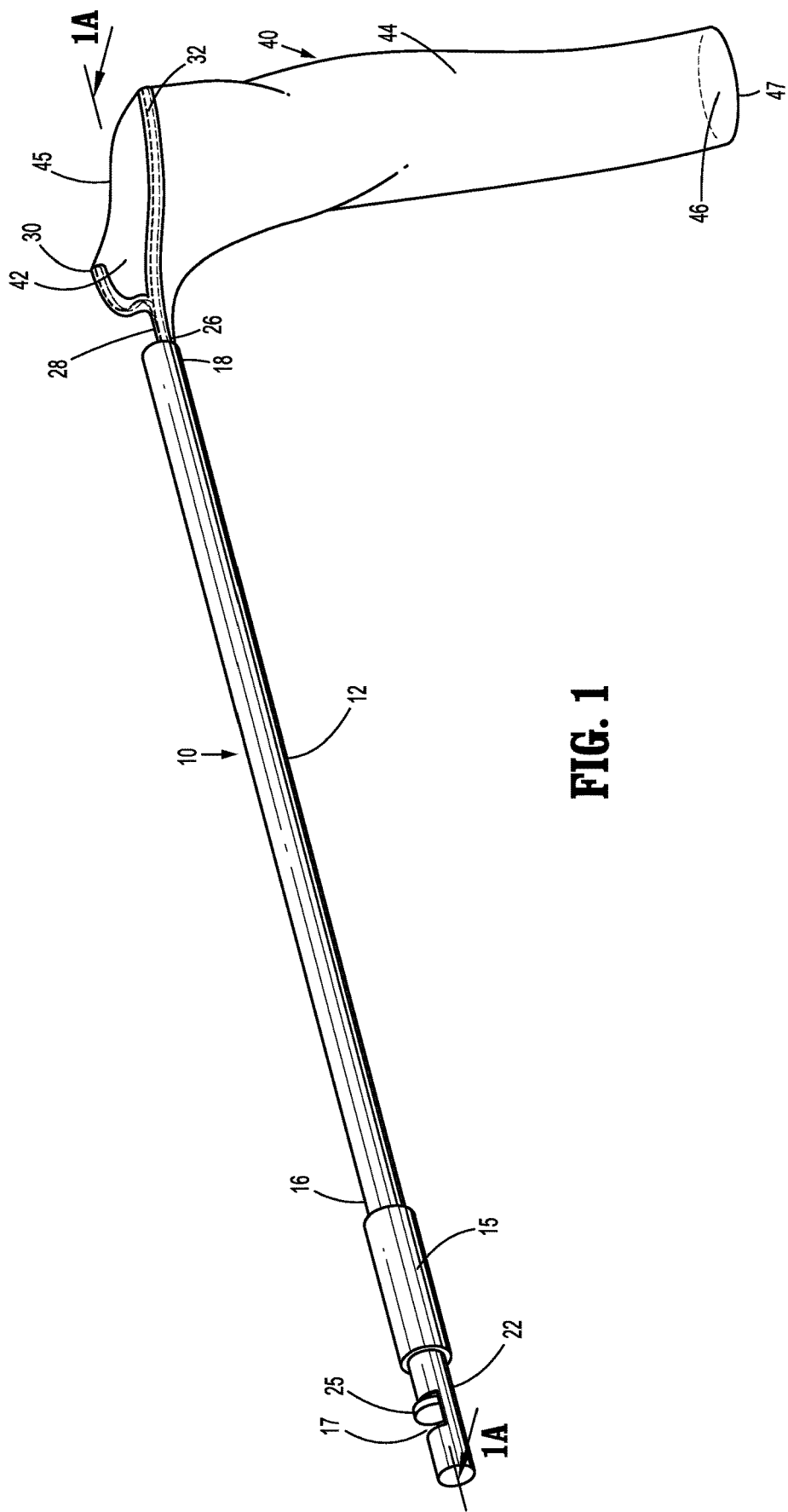
FIG. 1 is a side perspective view of a specimen retrieval device in accordance with an exemplary embodiment of the present disclosure in a non-articulated state.

The present disclosure provides a specimen retrieval device for use in minimally invasive and other surgical procedures such as other reduced-access surgical procedures, partially-open surgical procedures, and open surgical procedures. As used herein, minimally invasive surgical procedures encompass laparoscopic procedures, arthroscopic procedures, and endoscopic procedures, and refer to procedures utilizing scopes or similar devices having relatively narrow operating portions capable of insertion through a small incision in the skin.

The aspects of the present disclosure may be modified for use with various methods for retrieving tissue specimens during a surgical procedure and, in particular, a minimally invasive surgical procedure including, for example, cholecystectomies, appendectomies, nephrectomies, colectomies, splenectomies, laparoscopic hysterectomies, and the like.

The presently disclosed specimen retrieval device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. The term "clinician" is used generally to refer to medical personnel including doctors, surgeons, nurses, and support personnel.

Figure 2:
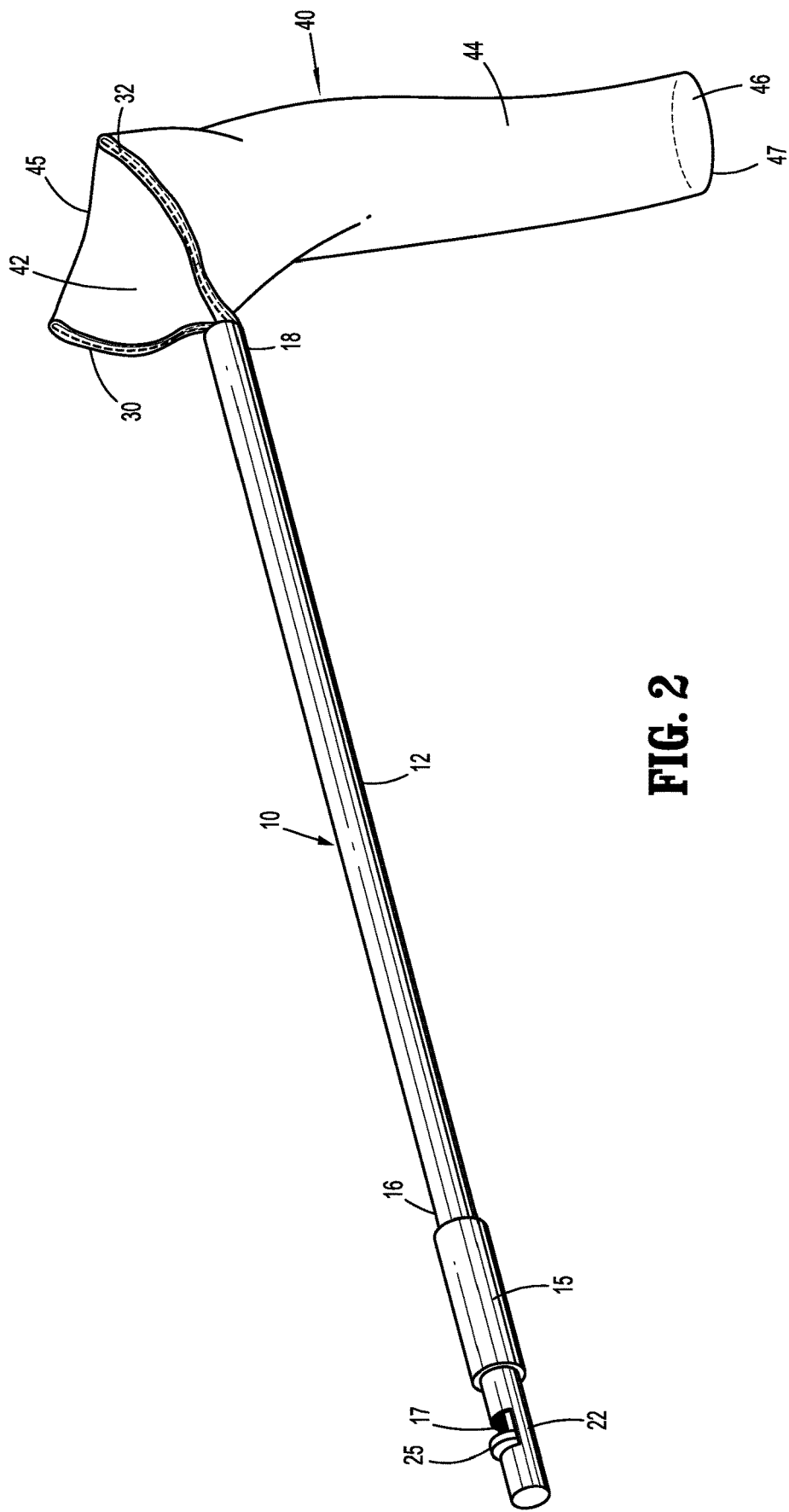
FIG. 2 is a side perspective view showing the specimen retrieval device shown in FIG. 1 in an articulated state.

Referring to FIGS. 1-4, and initially with reference to FIGS. 1-2, the specimen retrieval device 10 of the present disclosure includes a tubular body 12 having a proximal portion 16 and a distal portion 18, and defines a longitudinal bore 14 that extends between the proximal portion 16 and the distal portion 18. The tubular body 12 has a hand grip 15 thereon. The hand grip 15 on the tubular body 12 may be formed as a unitary component or as two separate half components that are coupled to one another about the tubular body 12 by one or more suitable coupling methods (e.g., one or more suitable adhesives).

The specimen retrieval device 10 also includes an articulation shaft assembly 20 (FIG. 1A) including an articulation shaft 22 rotatably positioned within the longitudinal bore 14 of the tubular body 12, and an articulation knob 25 accessible through an opening 17 in the tubular body 12 at a proximal portion 24 of the articulation shaft 22. The opening 17 permits access to, and manipulation of, the articulation knob 25 at the proximal portion 24 of the articulation shaft 22. The distal portion 18 of the tubular body 12 supports a support assembly 28 (FIG. 1) that provides support for a specimen receptacle 40. As shown in FIG. 1, the specimen receptacle 40 includes a body 44 having a generally tubular or elongated configuration that is defined by an openable and closable proximal portion (or mouth) 45 which defines a first opening 42. The specimen receptacle 40 also has a second mouth 47 defining a second opening 46 at a distance from the first opening 42. Alternatively, other specimen receptacle configurations are envisioned.

Figure 1A:
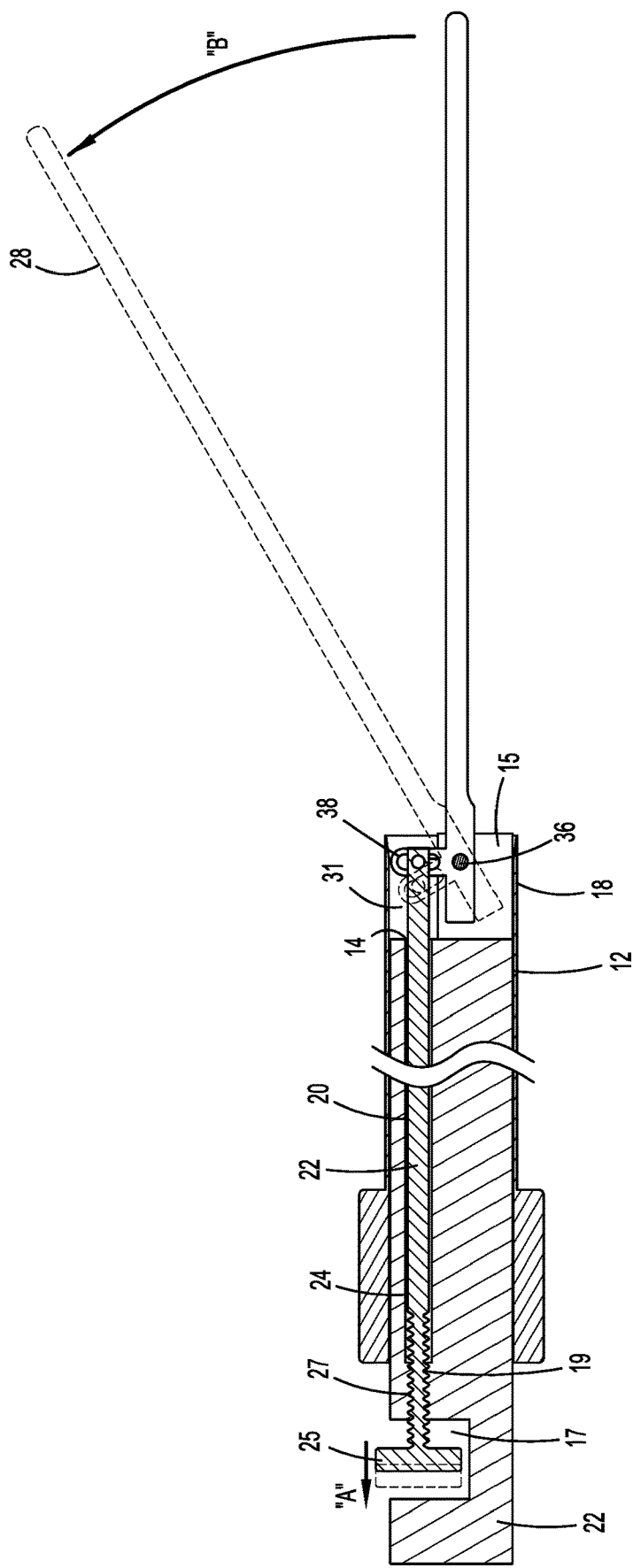
FIG. 1A is a cross-sectional view taken along section line 1A-1A of FIG. 1.

Turning to FIG. 1A, the articulation knob 25 is attached to the articulation shaft 22, which travels the length of the tubular body 12. The articulation shaft 22 has a threaded proximal portion 27 which is received in a threaded segment 19 of the longitudinal bore 14 such that rotation of the articulation shaft 22 causes longitudinal movement of the articulation shaft 22 within the longitudinal bore 14 of the tubular body 12.

A distal portion 31 of the articulation shaft 22 is attached to a tab 38 affixed to the support member 28. The support member 28 is affixed to the tubular body 12 by pin 36, which permits the support member 28 to pivot or articulate in relation to the pin 36. The distal portion 18 of tubular body 12 has an opening 15 that permits articulation of the support member 28.

The tubular body 12 and/or the articulation shaft assembly 22 of the present disclosure are made of biocompatible materials within the purview of those skilled in the art, in embodiments, polymeric materials. For example, the tubular body 12 and/or the articulation shaft assembly 22 may be made of thermoplastic polyurethanes sold under the name PELLETHANE®, which offer flexibility and a wide range of hardness. The tubular body 12 and/or the articulation shaft assembly 22, for example, may be fabricated from PELLETHANE® 2363-80A, PELLETHANE® 2363-90A, PELLETHANE® 2363-55D, any combination thereof, or any alternatives within the purview of those skilled in the art. In some embodiments, the tubular body 12 and the articulation shaft assembly 22 are formed of the same material. In other embodiments, the tubular body 12 and the articulation shaft assembly 22 are formed of different materials.

Figure 3:
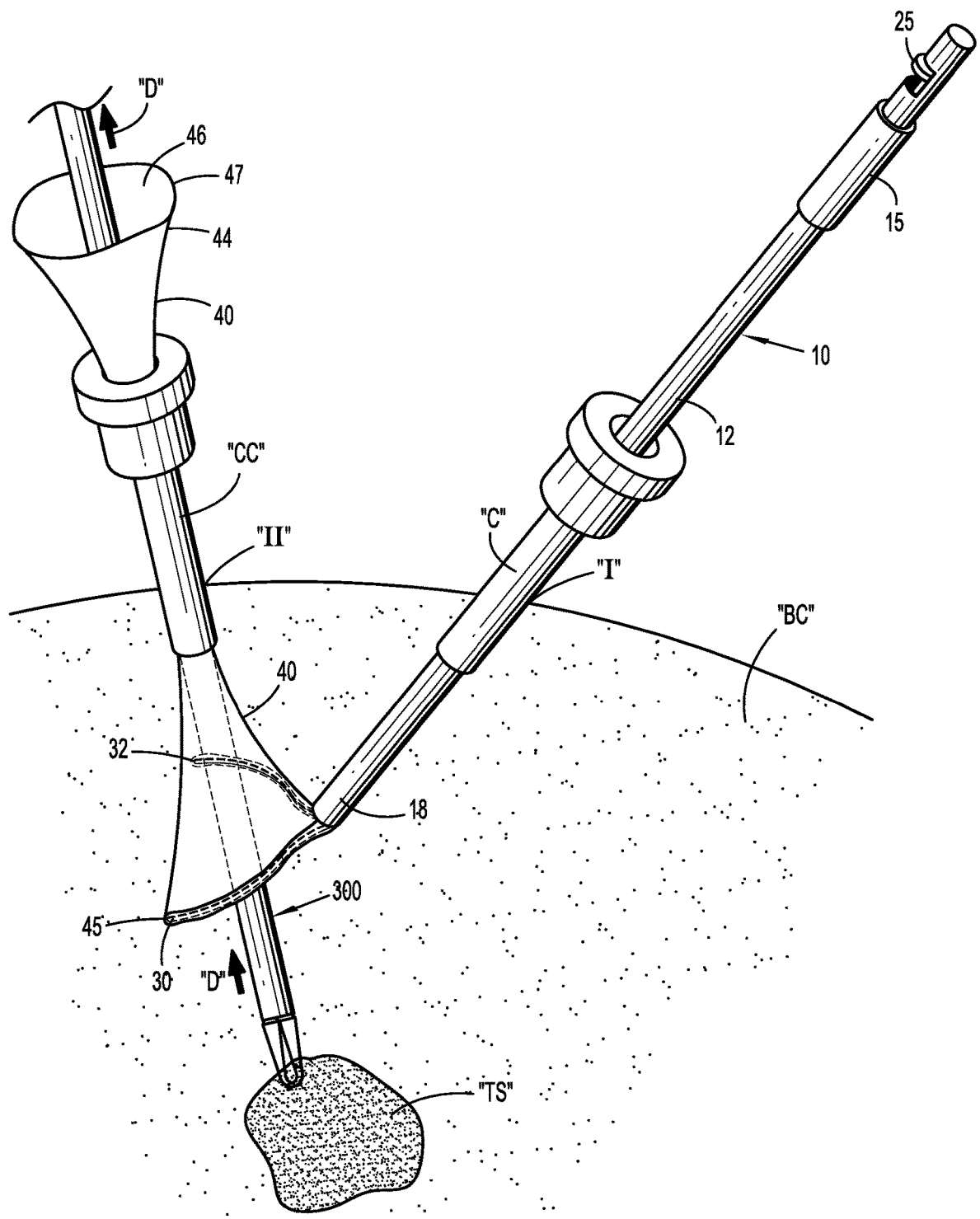
FIG. 3 is a side, perspective view of the specimen retrieval device shown in FIG. 1 in use.
Figure 4:
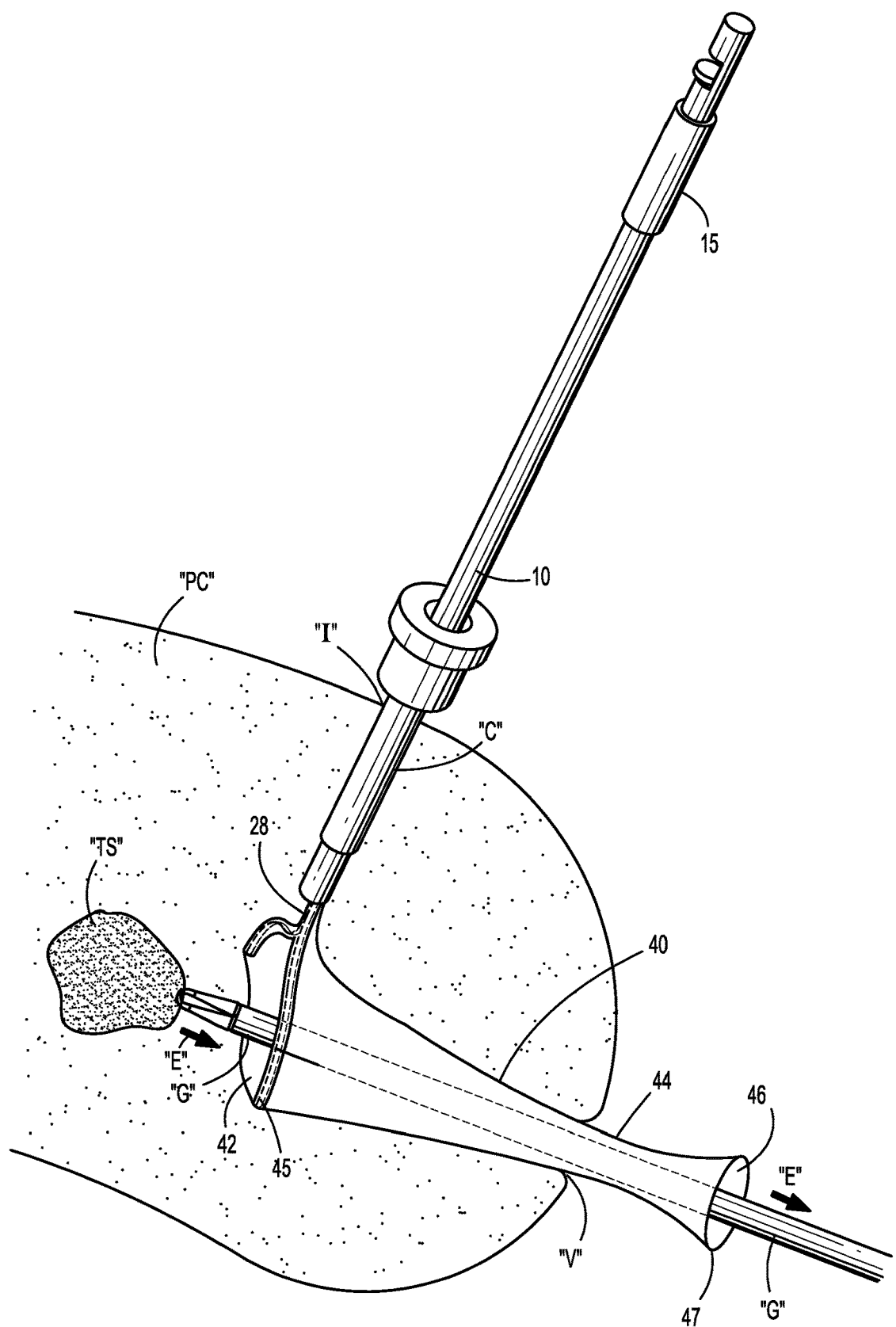
FIG. 4 is a side, perspective view of the specimen retrieval device shown in FIG. 1 in an alternate use.

As depicted in FIGS. 1 and 2, in embodiments, the support member 28 includes a pair of resilient fingers 30, 32 that extend distally from the opening 15 in the distal portion 18 of the tubular body 12. The resilient fingers 30, 32 are movable from a spaced non-deformed state (FIG. 1) to a deformed state (not shown) to facilitate placement of the specimen receptacle 40 into a patient's body, such as by passage through a cannula, delivery tube, or some similar device (FIGS. 3 and 4 depict introduction of the specimen retrieval device 10 through a cannula 100). The resilient fingers 30, 32 return to the non-deformed state when the specimen receptacle 40 is deployed into a patient's body to open the opening 42 of the specimen receptacle 40, as described below.

The body 44 of the specimen receptacle 40 may be made from any suitable biocompatible material (e.g., nylon, urethane, ripstop nylon or latex) capable of forming a flexible collapsible member, or membrane. In embodiments, the material from which the specimen receptacle is made is resilient, antistatic, pyrogen-free, non-toxic, and sterilizable. In embodiments, materials used to form the tubular body 12 and/or the inner shaft 22 described above may be used to form the specimen receptacle 40. In other embodiments, the specimen receptacle 40 is formed of materials that are different from those used to form the tubular body 12 and/or the inner shaft 22. The specimen receptacle 40 may be opaque or clear.

In embodiments, the resilient fingers 30, 32 may be received in a cuff (not shown) formed about the mouth 42 of the specimen receptacle 40. The cuff may be formed on the specimen receptacle 40 by any suitable method. In embodiments, for example, a top portion of the specimen receptacle 40 may be folded into an interior thereof or onto an exterior thereof and, subsequently, glued thereto to form the cuff.

In use, as shown in FIG. 1A, turning the articulation knob 25 in a counter-clockwise fashion moves the articulation shaft 22 in a proximal direction (indicated by arrow "A" in FIG. 1A), thereby pulling the tab 38 on the support member 28 in the proximal direction and causing articulation (sometimes referred to herein as "pivotable movement") of the support member 28 in the direction indicated by arrow "B" in FIG. 1A about a pivot axis in relation to the pin 36 at the distal portion 18 of the tubular body 12.

As depicted in FIGS. 1A and 2, the support member 28 of the specimen receptacle 40 is capable of articulating to facilitate placement of a tissue specimen within the specimen receptacle 40; FIG. 2 shows the specimen retrieval device 10 of the present disclosure in an articulated position.

In an assembled configuration, the hand grip 15 and the articulation knob 25 can be manipulated to facilitate manipulation of the specimen retrieval device 10 and the rotation of the articulation shaft 22 within the tubular body 12. More specifically, the hand grip 15 can be grasped by the clinician with one hand and the articulation knob 25 can be rotated by the clinician with the other hand to move the articulation shaft 22 within the tubular body 12.

In use, as depicted in FIG. 3, a first cannula 100 may be introduced through a first incision "I" for access to a patient's body cavity "BC." The resilient fingers 36, 38 of the support member 28 may be deformed to permit passage through the first cannula 100 (not shown) and the tubular body 12 of the specimen retrieval device 10 can be inserted through the first cannula 100 to position the specimen receptacle 40 in the body cavity "BC" adjacent a surgical site. Once present within the body cavity "BC," the resilient fingers 36, 38 open to their non-deformed state, thereby forming the first opening 42 of the specimen receptacle 40.

As shown in FIG. 3, a second cannula 200 may be introduced through a second incision "II", and a grasping device 300 (e.g., a tenaculum, forceps, etc.) may be used to remove the mouth 47 defining the second opening 46 of the body 44 of the specimen receptacle 40 by passing it through the second cannula 200. The articulation knob 25 may be rotated as described above with respect to FIG. 1A to articulate the support member 28 if necessary or desired. The grasping device 300 may then be introduced through the second opening 46 of the specimen receptacle 40, through the body 44 of the specimen receptacle 40, and through the first opening 42 of the specimen receptacle 40, at which point the graspers may be operated to grasp a tissue specimen "TS." FIG. 3 shows the support member 28 in an articulated position, which facilitates passage of the tissue specimen "TS" through the first opening 42 of the specimen receptacle 40, through the body 44 of the specimen receptacle 40, and out the second opening 46 of the body 44 of the specimen receptacle 40. Movement of the grasping device 300 in a proximal direction (depicted by arrow "D" in FIG. 3) will remove the tissue specimen "TS" through the specimen receptacle 40 and out of the patient's body cavity "BC."

In an alternate method of use, as depicted in FIG. 4, for a laparoscopic hysterectomy or a similar procedure where vaginal access is part of the procedure, the second opening 46 and a portion of the body 44 of the specimen receptacle 40 may pass through the vaginal opening "V." As depicted in FIG. 4, a cannula 100 may be introduced through an incision "I" for access to a patient's pelvic cavity "PC." The specimen retrieval device 10 may be inserted through the cannula 100. Once present within the pelvic cavity "PC," the resilient fingers 36, 38 open to their non-deformed state, thereby forming the first opening 42 of the specimen receptacle 40. The grasping device 300 may be used to remove the mouth 47 defining the second opening 46 of the body 44 of the specimen receptacle 40 by passing through the vaginal opening "V." FIG. 4 shows the support member 28 in an un-articulated position, which facilitates passage of a tissue specimen "TS" through the first opening 42 defined by the mouth 45 of the specimen receptacle 40, through the body 44 of the specimen receptacle 40, and out the second opening 46 of the body 44 of the specimen receptacle 40. Movement of the grasping device 300 in a proximal direction (depicted by arrow "E" in FIG. 4) will remove the tissue specimen "TS" through the specimen receptacle 40 and out of the patient's pelvic cavity "PC."

Where the tissue specimen "TS" is too large to be removed without first breaking it up into smaller pieces, a morcellator, tenaculum, (not shown) or similar device may be introduced through the first opening 42 and/or the second opening 46 to break up the tissue sample "TS" within the specimen receptacle 40 prior to its removal from the specimen receptacle 40 (not shown). Examples of such procedures, including the use of a tenaculum and radiofrequency (RF) energy to break up the tissue specimen, to aid in its removal from the specimen receptacle, are disclosed in U.S. Patent Application Publication No. 20160058495, the entire disclosure of which is incorporated by reference herein.

Kits of the present disclosure may include the specimen retrieval device described above, as well as trocars, grasping devices, vacuum sources (tubes), combinations thereof, and the like. In some embodiments, these additional devices, such as grasping devices and/or vacuum sources, may be used to break up the tissue specimen in the specimen receptacle prior to removing the specimen retrieval device from the body cavity.

Once the specimen retrieval device of the present disclosure has been removed from the patient's body, any tissue specimen "TS" may be removed from the specimen receptacle 40 for further examination and the specimen receptacle 40 may be discarded.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A method comprising:
introducing a tubular body of a specimen retrieval device having a proximal portion and a distal portion through a body opening into a body cavity;
introducing an articulation shaft having a proximal portion, a distal portion, and an articulation knob through a longitudinal bore of the tubular body such that the distal portion of the articulation shaft is coupled to a support member that is pivotably supported about a pivot axis on the distal portion of the tubular body;
positioning the distal portion of the tubular body within the body cavity to position a specimen receptacle supported on the support member in the body cavity;
actuating the articulation knob of the articulation shaft to articulate the support member about the pivot axis to reposition a first opening of the specimen receptacle in relation to a tissue specimen from a non-articulated position to an articulated position;
removing a second opening of the specimen receptacle from the body cavity;
passing the tissue specimen through the first opening of the specimen receptacle with the first opening in the articulated position into the specimen receptacle and out the second opening; and
removing the specimen retrieval device from the body cavity.

2. The method of claim 1, wherein introducing the specimen retrieval device through the body opening occurs by passing the distal portion of the tubular body through a cannula.

3. The method of claim 1, wherein actuating the articulation knob includes rotating a threaded portion of the articulation shaft within a threaded portion of the longitudinal bore to longitudinally move the articulation shaft, thereby articulating the support member.

4. The method of claim 1, wherein removing the second opening from the body cavity occurs by grasping the specimen receptacle with a grasping device and pulling the second opening out of the body cavity.

5. The method of claim 4, wherein the grasping device is selected from the group consisting of a forceps, a tenaculum, and combinations thereof.

6. The method of claim 4, wherein removing the second opening occurs by pulling the second opening out of a cannula.

7. The method of claim 4, wherein removing the second opening occurs by pulling the second opening out of a patient's vagina.

8. The method of claim 1, wherein the support member includes a pair of resilient fingers which support the specimen receptacle and open the first opening of the specimen receptacle in a deployed state.

9. The method of claim 8, wherein passing the tissue specimen through the first opening of the specimen receptacle into the specimen receptacle and out the second opening occurs by utilizing a grasping device to grasp the tissue specimen and pass the tissue specimen through the specimen receptacle.

10. The method of claim 9, wherein the grasping device is selected from the group consisting of a forceps, a tenaculum, and combinations thereof.

11. A method of performing a laparoscopic hysterectomy procedure comprising:
introducing a tubular body of a specimen retrieval device having a proximal portion and a distal portion through a body opening of a patient;
positioning the distal portion of the tubular body within a pelvic cavity of the patient;
deploying a support member of the specimen retrieval device from the tubular body into the pelvic cavity of the patient to deploy a specimen receptacle having a first opening and a second opening into the body cavity of the patient;
moving the support member from a non-articulated position to an articulated position to move the first opening of the specimen receptacle to an articulated position;
withdrawing a portion of the specimen receptacle defining the second opening from the pelvic cavity of the patient through a vaginal opening of the patient;
passing a tissue specimen through the first opening of the specimen receptacle into the specimen receptacle with the first opening of the specimen receptacle in the articulated position; and
removing the tissue specimen from the specimen receptacle through the second opening of the specimen receptacle and the vaginal opening of the patient; and
removing the specimen retrieval device from the pelvic cavity.

12. The method of claim 11, wherein withdrawing the portion of the specimen receptacle defining the second opening from the pelvic cavity of the patient through the vaginal opening of the patient occurs by grasping the specimen receptacle with a grasping device and pulling the second opening out of the vaginal opening.

13. The method of claim 12, wherein the grasping device is selected from the group consisting of a forceps, a tenaculum, and combinations thereof.

14. The method of claim 11, wherein passing the tissue specimen through the first opening of the specimen receptacle into the specimen receptacle and out the second opening occurs by utilizing a grasping device to grasp the tissue specimen and pass the tissue specimen through the specimen receptacle.

15. The method of claim 14, wherein the grasping device is selected from the group consisting of a forceps, a tenaculum, and combinations thereof.

* * * * *